(12) United States Patent
Smets et al.

(10) Patent No.: US 8,450,259 B2
(45) Date of Patent: May 28, 2013

(54) BENEFIT AGENT DELIVERY COMPOSITIONS

(75) Inventors: Johan Smets, Lubbeek (BE); Pascale Claire Annick Van Steenwinckel, Weerde (BE)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 12/872,480

(22) Filed: Aug. 31, 2010

(65) Prior Publication Data
US 2010/0331190 A1 Dec. 30, 2010

Related U.S. Application Data

(63) Continuation of application No. 12/286,467, filed on Sep. 30, 2008, now abandoned, which is a continuation of application No. 12/070,093, filed on Feb. 15, 2008, now abandoned.

(60) Provisional application No. 60/901,569, filed on Feb. 15, 2007.

(51) Int. Cl.
*C11D 1/10* (2006.01)

(52) U.S. Cl.
USPC ........... 510/276; 510/101; 510/361; 424/70.1

(58) Field of Classification Search
USPC .................. 510/101, 276, 361; 424/70.1
See application file for complete search history.

(56) References Cited

U.S. PATENT DOCUMENTS

| | | | |
|---|---|---|---|
| 4,076,663 A * | 2/1978 | Masuda et al. ............. 525/54.31 |
| 4,430,243 A | 2/1984 | Bragg |
| 4,515,705 A | 5/1985 | Moeddel |
| 4,537,706 A | 8/1985 | Severson, Jr. |
| 4,537,707 A | 8/1985 | Severson, Jr. |
| 4,550,862 A | 11/1985 | Barker et al. |
| 4,561,998 A | 12/1985 | Wertz et al. |
| 4,597,898 A | 7/1986 | Vander Meer |
| 4,968,451 A | 11/1990 | Scheibel et al. |
| 5,486,303 A | 1/1996 | Capeci et al. |
| 5,489,392 A | 2/1996 | Capeci et al. |
| 5,516,448 A | 5/1996 | Capeci et al. |
| 5,565,145 A | 10/1996 | Watson et al. |
| 5,565,422 A | 10/1996 | Del Greco et al. |
| 5,569,645 A | 10/1996 | Dinniwell et al. |
| 5,574,005 A | 11/1996 | Welch et al. |
| 5,574,179 A | 11/1996 | Wahl et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,879,584 A | 3/1999 | Bianchetti et al. |
| 5,929,022 A | 7/1999 | Velazquez |
| 6,217,889 B1 * | 4/2001 | Lorenzi et al. ................. 424/401 |
| 6,225,464 B1 | 5/2001 | Hiler, II et al. |
| 6,294,514 B1 | 9/2001 | Welling |
| 6,306,812 B1 | 10/2001 | Perkins et al. |
| 6,326,348 B1 | 12/2001 | Vinson et al. |
| 6,376,445 B1 | 4/2002 | Bettiol et al. |
| 6,451,751 B1 | 9/2002 | Busch et al. |
| 6,645,511 B2 * | 11/2003 | Aronson et al. ............... 424/401 |
| 6,740,713 B1 | 5/2004 | Busch et al. |
| 6,764,986 B1 | 7/2004 | Busch et al. |
| 6,972,276 B1 | 12/2005 | Besselievre et al. |
| 7,169,741 B2 | 1/2007 | Barry et al. |
| 7,297,674 B2 | 11/2007 | Hines |
| 2003/0228992 A1 * | 12/2003 | Smets et al. ................... 510/267 |
| 2004/0247664 A1 | 12/2004 | Dreja et al. |
| 2005/0130864 A1 | 6/2005 | Ouwendijk-Vrijenhoek et al. |
| 2005/0210601 A1 * | 9/2005 | Strang et al. ...................... 8/141 |
| 2006/0067963 A1 | 3/2006 | Bell |
| 2007/0196502 A1 | 8/2007 | Mort et al. |
| 2007/0202063 A1 * | 8/2007 | Dihora et al. ................. 424/70.1 |
| 2007/0275866 A1 | 11/2007 | Dykstra |
| 2008/0194454 A1 | 8/2008 | Morgan et al. |
| 2008/0200359 A1 * | 8/2008 | Smets et al. ................... 510/119 |
| 2009/0048351 A1 * | 2/2009 | Smets et al. ............... 514/772.4 |
| 2009/0209661 A1 * | 8/2009 | Somerville Roberts et al. .......................... 514/772.5 |
| 2010/0261629 A1 * | 10/2010 | Smets et al. ................... 510/107 |

FOREIGN PATENT DOCUMENTS

| | | |
|---|---|---|
| GB | 2 381 001 A | 4/2003 |
| WO | WO 00/32601 A2 | 6/2000 |

OTHER PUBLICATIONS

International Search Report, date mailed Jul. 4, 2008, International Application No. PCT/US2008/002120.

* cited by examiner

*Primary Examiner* — Mark Eashoo
*Assistant Examiner* — M. Reza Asdjodi
(74) *Attorney, Agent, or Firm* — Marianne Dressman; James F. McBride

(57) ABSTRACT

Benefit agent delivery compositions, compositions, packaged products and displays comprising such benefit agent delivery compositions, and processes for making and using such benefit agent delivery compositions, compositions, packaged products and displays. Such compositions have improved deposition and retention properties that may impart improved benefit characteristics to a composition and/or situs.

7 Claims, No Drawings

BENEFIT AGENT DELIVERY COMPOSITIONS

CROSS-REFERENCES TO RELATED APPLICATIONS

This application is a continuation of and claims priority under 35 U.S.C. §120 to U.S. patent application Ser. No. 12/286,467, filed Sep. 30, 2008, now abandoned which in turn is a continuation of and claims priority under 35 U.S.C. §120 to U.S. patent application Ser. No. 12/070,093, filed Feb. 15, 2008, now abandoned which claims priority under 35 U.S.C. §119(e) to U.S. Provisional Application Ser. No. 60/901,569 filed Feb. 15, 2007.

FIELD OF INVENTION

The present application relates to benefit agent delivery compositions, compositions, packaged products and displays comprising such benefit agent delivery compositions, and processes for making and using such benefit agent delivery compositions and compositions, packaged products and displays comprising such benefit agent delivery compositions.

BACKGROUND OF THE INVENTION

Benefit agents, such as perfumes, brighteners, insect repellants, silicones, waxes, flavors, vitamins and fabric softening agents, skin care agents are expensive and may be less effective when employed at high levels in personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost do to the agents' physical or chemical characteristics, such agents may be incompatible with other compositional components or the situs that is treated, or such agents may be lost during post application processes such as rinsing or drying.

Accordingly, there is a need for a benefit agent delivery composition that provides improved benefit agent delivery efficiency. While not being bound by theory, applicants believe that the benefit agent delivery compositions disclosed herein meet such need as such compositions have increased deposition and retention properties which result in the desired increase in benefit agent delivery efficiency.

SUMMARY OF THE INVENTION

Benefit agent delivery compositions, compositions, packaged products and displays comprising such benefit agent delivery compositions, and processes for making and using such benefit agent delivery compositions, and compositions, packaged products and displays comprising such benefit agent delivery compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations there of.

As used herein, the term "amine" includes, unless otherwise indicated, primary, secondary, tertiary, and quaternary amines.

As used herein, the articles such as "a" and "an" when used in a claim, are understood to mean one or more of what is claimed or described.

As used herein, the terms "include", "includes" and "including" are meant to be synonymous with the phrase "including but not limited to".

As used herein, the term "solid" includes granular, powder, bar and tablet product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Benefit Agent Delivery Compositions

In one aspect, benefit agent delivery compositions comprising a benefit agent, a polymeric material and an optional cross-linker are disclosed.

Such benefit agent delivery compositions may comprise from about 5% to about 95%, from about 30% to about 85%, or even from about 40% to about 60% of a benefit agent; from about 5% to about 70%, from about 20 to about 60%, or even from about 30% to about 55% of a polymeric compound containing a carboxylic acid moiety; and from about 0% to about 50%, from about 0% to about 10%, or even from about 1% to about 7% by weight of a cross-linking agent.

Suitable benefit agents include silicones, enzymes, fragrances, perfumes, perfume raw materials, fragrance raw materials, deodorants, odor counteractants, malodors, essential oils, ethers, esters, ketones, alcohols, glycols, silicone hydrocarbons, cyclic hydrocarbons, aldehydes, terpines, volatile or nonvolatile insecticides, volatile or nonvolatile insect repellants, volatile or nonvolatile pesticides, volatile or nonvolatile antimicrobial agents, volatile or nonvolatile fungicides, volatile or nonvolatile herbicides and mixtures thereof. In one aspect, the inclusion of volatile or nonvolatile acids is avoided to reduce the potential of the cross reaction of the acid with the cross-linker.

In one aspect, the benefit agent comprises a perfume raw material, a fragrance, a perfume, an essential oil, an insecticide, an insect repellant, a pesticide, a herbicide, an odorant, a malodor counteractant, an odor masking agent, a cooling agent, a vitamin, softening agent, a skin care agent, a silicone, a softening agent, an encapsulated perfume and combinations thereof.

In one aspect, the benefit agent comprises a fragrance and/or a perfume. Useful perfume materials include materials selected from the group consisting of Table 1 Perfumes, Table 2 Perfumes, Table 3 Perfumes and mixtures thereof.

TABLE 1

Perfumes

| Number | Registry Name | Trade Name |
|---|---|---|
| 1 | Propanoic acid, ethyl ester | Ethyl Propionate |
| 2 | Acetic acid, 2-methylpropyl ester | Isobutyl Acetate |
| 3 | Butanoic acid, ethyl ester | Ethyl Butyrate |
| 4 | Butanoic acid, 2-methyl-, ethyl ester | Ethyl-2-Methyl Butyrate |
| 5 | 2-Hexenal, (E)- | 2-Hexenal |
| 6 | 1-Butanol, 3-methyl-, acetate | Iso Amyl- Acetate |
| 7 | 2-Buten-1-ol, 3-methyl-, acetate | Prenyl Acetate |
| 8 | 2-Hexen-1-ol | Beta Gamma Hexenol |
| 9 | 3-Hexen-1-ol | Beta Gamma Hexenol |
| 10 | Benzaldehyde | Benzaldehyde |
| 11 | 3-Hexen-1-ol, acetate, (Z)- | Cis 3 Hexenyl Acetate |
| 12 | Benzoic acid, methyl ester | Methyl Benzoate |
| 13 | Benzeneacetaldehyde | Phenyl Acetaldehyde |
| 14 | Benzeneacetic acid, methyl ester | Methyl Phenyl Acetate |
| 15 | 1,3-Dioxolane-2-acetic acid, 2-methyl-, ethyl ester | Fructone |
| 16 | Benzeneacetaldehyde, .alpha.-methyl- | Hydratropic Aldehyde |
| 17 | 3-Cyclohexene-1-carboxaldehyde, 3,5-dimethyl- | Cyclal C, |
| 18 | Acetic acid, (2-methylbutoxy)-, 2-propenyl ester | Allyl Amyl Glycolate |
| 19 | Benzenemethanol, .alpha.-methyl-, acetate | Methyl Phenyl Carbinyl Acetate |
| 20 | Acetic acid, (3-methylbutoxy)-, 2-propenyl ester | Allyl Amyl Glycolate |
| 21 | Benzaldehyde, 4-methoxy- | Anisic Aldehyde |
| 22 | Benzeneacetic acid, ethyl ester | Ethyl Phenyl Acetate |
| 23 | 2-Cyclohexen-1-one, 2-methyl-5-(1-methylethenyl)-, (R)- | Laevo Carvone |
| 24 | Ethanol, 2,2'-oxybis- | Calone 161 |
| 25 | Acetic acid, 2-phenylethyl ester | Phenyl Ethyl Acetate |
| 26 | Benzoic acid, 2-amino-, methyl ester | Methyl Anthranilate |
| 27 | 4,7-Methano-1H-inden-6-ol, 3a,4,5,6,7,7a-hexahydro-, acetate | Flor Acetate |
| 28 | Octanal, 7-hydroxy-3,7-dimethyl- | Hydroxycitronellal |
| 29 | 2(3H)-Furanone, 5-ethyldihydro- | Gamma Hexalactone |
| 30 | Phenol, 4-methyl- | Para Cresol |
| 31 | Bicyclo[2.2.1]heptan-2-one, 1,7,7-trimethyl-, (1R)- | Camphor Gum |
| 32 | 2H-Pyran, 3,6-dihydro-4-methyl-2-(2-methyl-1-propenyl)- | Nerol Oxide |
| 33 | Benzeneethanol, .beta.-methyl- | Hydratropic Alcohol |
| 34 | Benzeneethanol, .alpha.,.alpha.-dimethyl- | Dimethyl Benzyl Carbinol |
| 35 | Benzoic acid, 2-(methylamino)-, methyl ester | Dimethyl Anthranilate |
| 36 | 2-Propenal, 3-phenyl- | Cinnamic Aldehyde |
| 37 | 2-Propenoic acid, 3-phenyl-, methyl ester | Methyl Cinnamate |
| 38 | 4H-Pyran-4-one, 2-ethyl-3-hydroxy- | Ethyl Maltol |
| 39 | Acetic acid ethyl ester | Ethyl Acetate |

TABLE 1-continued

Perfumes

| Number | Registry Name | Trade Name |
|---|---|---|
| 40 | 2-Heptanone | Methyl Amyl Ketone |
| 41 | Acetic acid, pentyl ester | Iso Amyl- Acetate |
| 42 | 3-Octanone | Ethyl Amyl Ketone |
| 43 | 2-Octanone | Methyl Hexyl Ketone |
| 44 | Heptenone, methyl- | Methyl Heptenone |
| 45 | 1-Heptanol | Heptyl Alcohol |
| 46 | 5-Hepten-2-one, 6-methyl- | Methyl Heptenone |
| 47 | Butanoic acid, 3-oxo-, ethyl ester | Ethyl Acetoacetate |
| 48 | Ethanol, 2-(2-methoxyethoxy)- | Veramoss Sps |
| 49 | Tricyclo[2.2.1.02,6]heptane, 1-ethyl-3-methoxy- | Neoproxen |
| 50 | Benzene, 1,4-dimethoxy- | Hydroquinone Dimethyl Ether |
| 51 | Carbonic acid, 3-hexenyl methyl ester, (Z)- | Liffarome |
| 52 | Oxirane, 2,2-dimethyl-3-(3-methyl-2,4-pentadienyl)- | Myroxide |
| 53 | Ethanol, 2-(2-ethoxyethoxy)- | Diethylene Glycol Mono Ethylether |
| 54 | Cyclohexaneethanol | Cyclohexyl Ethyl Alcohol |
| 55 | 3-Octen-1-ol, (Z)- | Octenol Dix |
| 56 | 3-Cyclohexene-1-carboxaldehyde, 3,6-dimethyl- | Clovertal |
| 57 | 1,3-Oxathiane, 2-methyl-4-propyl-, cis- | Oxane |
| 58 | Acetic acid, 4-methylphenyl ester | Para Cresyl Acetate |
| 59 | Benzene, (2,2-dimethoxyethyl)- | Phenyl Acetaldehyde Dimethyl Acetal |
| 60 | Ethanone, 1-(4-methylphenyl)- | Para Methyl Acetophenone |
| 61 | Propanoic acid, phenylmethyl ester | Benzyl Propionate |
| 62 | Octanal, 7-methoxy-3,7-dimethyl- | Methoxycitronellal Pq |
| 63 | Linalool oxide | Linalool Oxide |
| 64 | 2H-1-Benzopyran-2-one, octahydro- | Octahydro Coumarin |
| 65 | Benzenepropanal, .beta.-methyl- | Trifernal |
| 66 | 4,7-Methano-1H-indenecarboxaldehyde, octahydro- | Formyltricyclodecan |
| 67 | 2-Butanone, 4-phenyl- | Benzyl Acetone |
| 68 | Ethanone, 1-(4-methoxyphenyl)- | Para Methoxy Acetophenone |
| 69 | Benzoic acid, 2-hydroxy-, methyl ester | Methyl Salicylate USP |
| 70 | Propanenitrile, 3-(3-hexenyloxy)-, (Z)- | Parmanyl |
| 71 | 1,4-Methanonaphthalen-5(1H)-one, 4,4a,6,7,8,8a-hexahydro- | Tamisone |
| 72 | Benzene, [2-(2-propenyloxy)ethyl]- | LRA 220 |
| 73 | Benzenepropanol | Phenyl Propyl Alcohol |
| 74 | Ethanol, 2-phenoxy- | Phenoxyethanol |
| 75 | 1H-Indole | Indole |
| 76 | 1,3-Dioxolane, 2-(phenylmethyl)- | Ethylene Glycol Acetal/Phenyl Acetaldehy |
| 77 | 2H-1-Benzopyran-2-one, 3,4-dihydro- | Dihydrocoumarin |

In one aspect, suitable Table 1 perfume raw materials include perfume raw materials from number 1 to number 39 and mixtures thereof.

In one aspect, suitable Table 1 perfume raw materials include perfume raw materials from number 1 to number 29 and mixtures thereof.

In one aspect, suitable perfume raw materials having boiling point less than or equal to 250° C. and a ClogP greater than 2.5 are those materials listed in Table 2 below and such materials are defined as Table 2 perfume raw materials.

TABLE 2

Perfumes

| Number | Registry Name | Trade Name |
|---|---|---|
| 1 | Bicyclo[2.2.1]heptane, 2,2-dimethyl-3-methylene- | Camphene |
| 2 | Bicyclo[3.1.1]heptane, 6,6-dimethyl-2-methylene-, (1S)- | Beta Pinene |
| 3 | Bicyclo[3.1.1]hept-2-ene, 2,6,6-trimethyl- | Alpha Pinene |
| 4 | Propanoic acid, pentyl ester | Amyl Propionate |
| 5 | 1,6-Octadiene, 7-methyl-3-methylene- | Myrcene |
| 6 | Cyclohexene, 1-methyl-4-(1-methylethenyl)- | Dipentene |
| 7 | Cyclohexene, 1-methyl-4-(1-methylethenyl)- | Terpineolene |
| 8 | Acetic acid, hexyl ester | Hexyl Acetate |

TABLE 2-continued

Perfumes

| Number | Registry Name | Trade Name |
|---|---|---|
| 9 | Cyclohexene, 1-methyl-4-(1-methylethylidene)- | Terpineolene |
| 10 | Benzene, 1-methoxy-4-methyl- | Para Cresyl Methyl Ether |
| 11 | 1-Octen-3-ol, acetate | Amyl Vinyl Carbinyl Acetate |
| 12 | Octanal | Octyl Aldehyde |
| 13 | 2-Oxabicyclo[2.2.2]octane, 1,3,3-trimethyl- | Eucalyptol |
| 14 | Butanoic acid, pentyl ester | Amyl Butyrate |
| 15 | Heptanoic acid, ethyl ester | Ethyl Oenanthate |
| 16 | 5-Heptenal, 2,6-dimethyl- | Melonal |
| 17 | Hexanoic acid, 2-propenyl ester | Allyl Caproate |
| 18 | 3-Cyclohexene-1-carboxaldehyde, dimethyl- | Ligustral |
| 19 | 3-Hexene, 1-(1-ethoxyethoxy)-, (Z)- | Leaf Acetal |
| 20 | Octanal, 3,7-dimethyl- | Dihydrocitronellal |
| 21 | 2-Octynoic acid, methyl ester | Methyl Heptine Carbonate |
| 22 | 2-Nonenal | 2 Nonen-1-al |
| 23 | 1,6-Octadien-3-ol, 3,7-dimethyl- | Linalool |
| 24 | Benzoic acid, ethyl ester | Ethyl Benzoate |
| 25 | 6-Octenal, 3,7-dimethyl- | Citronellal |
| 26 | Cyclohexanol, 1-methyl-4-(1-methylethyl)- | Dihydroterpineol |
| 27 | 1-Hexanol, 3,5,5-trimethyl-, acetate | Iso Nonyl Acetate |
| 28 | 3,5-Octadien-2-ol, 2,6-dimethyl-, (?,Z)- | Muguol |
| 29 | Cyclohexanone, 5-methyl-2-(1-methylethyl)-, cis- | Iso Menthone |
| 30 | Heptanoic acid, 2-propenyl ester | Allyl Heptoate |
| 31 | Butanoic acid, 3-hexenyl ester, (Z)- | Cis 3 Hexenyl Butyrate |
| 32 | 1,6-Octadien-3-ol, 3,7-dimethyl-, formate | Linalyl Formate |
| 33 | 3-Cyclohexen-1-ol, 4-methyl-1-(1-methylethyl)- | Terpinenol |
| 34 | Bicyclo[2.2.1]heptan-2-ol, 1,3,3-trimethyl- | Fenchyl Alcohol |
| 35 | Cyclohexanol, 2-(1,1-dimethylethyl)-, cis- | Verdol |
| 36 | 3-Octanol, 3,7-dimethyl-, acetate | Tetrahydro Linayl Acetate |
| 37 | Bicyclo[2.2.1]heptan-2-ol, 1,7,7-trimethyl-, (1S-endo)- | Borneol Crystals |
| 38 | Decanal | Decyl Aldehyde |
| 39 | 3-Cyclohexene-1-methanol, .alpha.,.alpha.,4-trimethyl- | Alpha Terpineol |
| 40 | Cyclohexanol, 5-methyl-2-(1-methylethyl)- | Menthol |
| 41 | 3-Cyclohexene-1-carboxaldehyde, 2,4,6-trimethyl- | Iso Cyclo Citral |
| 42 | 7-Octen-2-ol, 2,6-dimethyl-, acetate | Dihydro Terpinyl Acetate |
| 43 | 2H-Pyran-2-one, 6-butyltetrahydro- | Nonalactone |
| 44 | 3-Hepten-2-one, 3,4,5,6,6-pentamethyl- | Koavone |
| 45 | 1,6-Nonadien-3-ol, 3,7-dimethyl- | Ethyl Linalool |
| 46 | 4-Decenal, (E)- | Decenal (Trans-4) |
| 47 | Terpineol | Terpineol |
| 48 | 7-Octen-2-ol, 2-methyl-6-methylene-, acetate | Myrcenyl Acetate |
| 49 | 2-Butenoic acid, 2-methyl-, 3-hexenyl ester, (E,Z)- | Cis-3-Hexenyl Tiglate |
| 50 | 1,6-Octadien-3-ol, 3,7-dimethyl-, acetate | Linalyl Acetate |
| 51 | Benzene, 1-methoxy-4-(1-propenyl)-, (E)- | Anethol Usp |
| 52 | 2-Decenal | 2 Decene-1-al |
| 53 | 2,6-Octadienal, 3,7-dimethyl- | Citral |
| 54 | 6-Octen-1-ol, 3,7-dimethyl-, formate | Citronellyl Formate |
| 55 | Cyclopentanone, 3-methyl-2-pentyl- | Jasmylone |
| 56 | Undecenal | Iso C-11 Aldehyde |
| 57 | 6-Octen-1-ol, 3,7-dimethyl- | Citronellol |
| 58 | Cyclohexanemethanol, .alpha.,.alpha.,4-trimethyl-, acetate | Dihydro Terpinyl Acetate |
| 59 | 3-Cyclohexene-1-methanol, .alpha.,.alpha,4-trimethyl-, acetate | Terpinyl Acetate |
| 60 | 2,6-Octadien-1-ol, 3,7-dimethyl-, formate, (E)- | Geranyl Formate |
| 61 | Bicyclo[2.2.1]heptan-2-ol, 1,3,3-trimethyl-, acetate | Fenchyl Acetate |
| 62 | Bicyclo[2.2.1]heptan-2-ol, 1,7,7-trimethyl-, acetate, exo- | Iso Bornyl Acetate |

TABLE 2-continued

Perfumes

| Number | Registry Name | Trade Name |
|---|---|---|
| 63 | 2,6-Octadien-1-ol, 3,7-dimethyl-, (E)- | Geraniol |
| 64 | 2,6-Octadien-1-ol, 3,7-dimethyl-, (Z)- | Nerol |
| 65 | Cyclohexanol, 2-(1,1-dimethylethyl)-, acetate | Verdox |
| 66 | Undecanal, 2-methyl- | Methyl Nonyl Acetaldehyde |
| 67 | Undecanal | Undecyl Aldehyde |
| 68 | 2H-Pyran-2-one, tetrahydro-6-pentyl- | Delta Decalactone |
| 69 | 6-Octen-1-ol, 3,7-dimethyl-, acetate | Citronellyl Acetate |
| 70 | 10-Undecenal | Intreleven Aldehyde Sp |
| 71 | 2(3H)-Furanone, 5-hexyldihydro- | Gamma Decalactone |
| 72 | 2,6-Octadien-1-ol, 3,7-dimethyl-, acetate, (E)- | Geranyl Acetate |
| 73 | 2H-Pyran-2-one, tetrahydro-6-(3-pentenyl)- | Jasmolactone |
| 74 | Cyclohexanol, 5-methyl-2-(1-methylethyl)-, acetate,(1.alpha.,2.beta.,5.alpha.)- | Menthyl Acetate |
| 75 | 2-Undecenal | 2-Undecene-1-Al |
| 76 | 2H-Pyran-2-one, tetrahydro-6-(2-pentenyl)-, (Z)- | Jasmolactone |
| 77 | 2,6-Octadien-1-ol, 3,7-dimethyl-, acetate, (Z)- | Neryl Acetate |
| 78 | Benzeneethanol, .alpha.,.alpha.-dimethyl-, acetate | Dimethyl Benzyl Carbinyl Acetate |
| 79 | 4,9-Decadienal, 4,8-dimethyl- | Floral Super |
| 80 | 3-Octanol | Octanol-3 |
| 81 | 2-Heptanol, 2,6-dimethyl- | Dimethyl-2, 6-Heptan-2-ol |
| 82 | Propanoic acid, 2-methyl-, 1,3-dimethyl-3-butenyl ester | Iso Pentyrate |
| 83 | 3-Nonanone | Ethyl Hexyl Ketone |
| 84 | 2,4,6-Octatriene, 2,6-dimethyl- | Allo-Ocimene |
| 85 | Bicyclo[2.2.1]heptane, 2-ethyl-5-methoxy- | Neoproxen |
| 86 | 1-Octanol | Octyl Alcohol |
| 87 | 3-Octanol, 3,7-dimethyl- | Linacsol |
| 88 | Propanoic acid, 2-methyl-, 3-hexenyl ester, (Z)- | Verdural B Extra |
| 89 | 2H-Pyran, tetrahydro-4-methyl-2-(2-methyl-1-propenyl)- | Methyl Iso Butenyl Tetrahydro Pyran |
| 90 | Nonanal | Nonyl Aldehyde |
| 91 | Hexanoic acid, 2-methylpropyl ester | Iso Butyl Caproate |
| 92 | Cyclohexane, 3-ethoxy-1,1,5-trimethyl- | Herbavert |
| 93 | 7-Octen-2-ol, 2-methyl-6-methylene-, dihydro deriv. | Dihydro Myrcenol |
| 94 | Ethanone, 1-(3,3-dimethylcyclohexyl)- | Herbac |
| 95 | Propanoic acid, 2,2-dimethyl-, hexyl ester | Hexyl Neo Pentanoate |
| 96 | 3-Heptanone, 5-methyl-, oxime | Stemone |
| 97 | Isononanol | Iso Nonyl Alcohol |
| 98 | Cyclohexanone, 2-(1-methylpropyl)- | 2-Sec-Butyl Cyclo Hexanone |
| 99 | Butanoic acid, 2-methyl-, hexyl ester | Hexyl-2-Methyl Butyrate |
| 100 | 1-Nonanol | Nonyl Alcohol |
| 101 | Cyclohexaneethanol, acetate | Cyclohexyl Ethyl Acetate |
| 102 | 1-Octanol, 3,7-dimethyl- | Dimethyl Octanol |
| 103 | Cyclopentanone, 2-pentyl- | Delphone |
| 104 | Cyclohexanemethanol, 4-(1-methylethyl)-, cis- | Mayol |
| 105 | 6-Octen-1-ol, 3,7-dimethyl-, (S)- | Baranol |
| 106 | Benzaldehyde, 4-(1-methylethyl)- | Cuminic Aldehyde |
| 107 | Propanoic acid, 2-methyl-, phenylmethyl ester | Benzyl Iso Butyrate |
| 108 | Propanoic acid, 2-methyl-, 4-methylphenyl ester | Para Cresyl Iso Butyrate |
| 109 | Carbonic acid, 4-cycloocten-1-yl methyl ester | Violiff |
| 110 | 1,6-Octadien-3-ol, 3,7-dimethyl-, propanoate | Linalyl Propionate |
| 111 | Cyclohexanemethanol, .alpha.-methyl-4-(1-methylethyl)- | Mugetanol |
| 112 | Butanoic acid, phenylmethyl ester | Benzyl Butyrate |
| 113 | 4,7-Methano-1H-inden-5-ol, octahydro-, acetate | Dihydro Cyclacet |
| 114 | 2-Cyclopenten-1-one, 3-methyl-2-pentyl- | Dihydrojasmone |
| 115 | Bicyclo[2.2.1]heptan-2-ol, 1,7,7-trimethyl-, propanoate, exo- | Iso Bornyl Propionate |

TABLE 2-continued

Perfumes

| Number | Registry Name | Trade Name |
|---|---|---|
| 116 | 2,6-Octadienenitrile, 3,7-dimethyl- | Geranyl Nitrile |
| 117 | Benzene, ethenyl- | Styrene |
| 118 | Benzene, methyl(1-methylethyl)- | Cymene Coeur |
| 119 | Cyclohexanol, 3,3,5-trimethyl-, cis- | Trimethylcyclohexanol |
| 120 | 1-Hexanol, 5-methyl-2-(1-methylethyl)-, (R)- | Tetrahydro Lavandulol |
| 121 | Cyclohexanel, 4-(1-methylethyl)- | Roselea |
| 122 | 7-Octen-2-ol, 2,6-dimethyl-, formate | Dimyrcetol |
| 123 | Cyclohexanone, 5-methyl-2-(1-methylethyl)-, trans- | Menthone Racemic |
| 124 | 1,3,5-Undecatriene | Galbanolene Super |
| 125 | 5,7-Octadien-2-ol, 2,6-dimethyl- | Ocimenol |
| 126 | 2-Cyclohexene-1-carboxylic acid, 2,6,6-trimethyl-, methyl ester | Methyl Cyclogeranate |
| 127 | Benzene, (2-bromoethenyl)- | Brom Styrol |
| 128 | Benzene, 1-methoxy-4-(2-propenyl)- | Methyl Chavicol |
| 129 | 2H-Pyran, 6-butyl-3,6-dihydro-2,4-dimethyl- | Gyrane |
| 130 | Cyclohexanemethanol, .alpha.,3,3-trimethyl-, formate | Aphermate |
| 131 | Cyclohexanol, 4-(1,1-dimethylethyl)- | Patchon |
| 132 | Cyclohexanol, 5-methyl-2-(1-methylethyl)-, [1R-(1.alpha.,2.beta.,5.alpha.)]- | Menthol Natural |
| 133 | 1,3-Dioxane, 2-butyl-4,4,6-trimethyl- | Herboxane |
| 134 | 2-Nonynoic acid, methyl ester | Methyl Octine Carbonate |
| 135 | 6-Octenenitrile, 3,7-dimethyl- | Baranyl Nitrile |
| 136 | Decanal, 2-methyl- | Methyl Octyl Acetaldehyde |
| 137 | 2-Nonanol, 6,8-dimethyl- | Nonadyl |
| 138 | Phenol, 4-(1,1-dimethylethyl)- | Para Tertiary Butyl Phenol |
| 139 | 1-Hexanol, 5-methyl-2-(1-methylethyl)-, acetate | Tetrahydro Lavandulyl Acetate |
| 140 | Cyclohexanol, 5-methyl-2-(1-methylethenyl)-, [1R-(1.alpha.,2.beta.,5.alpha.)]- | Iso Pulegol |
| 141 | Cyclohexanone, 4-(1,1-dimethylpropyl)- | Orivone |
| 142 | 2-Undecanone | Methyl Nonyl Ketone |
| 143 | Cyclohexanemethanol, .alpha.,3,3-trimethyl-, acetate | Rosamusk |
| 144 | 3-Cyclohexene-1-methanol, 2,4,6-trimethyl- | Isocyclogeraniol |
| 145 | 2,6-Octadiene, 1,1-dimethoxy-3,7-dimethyl- | Citral Dimethyl Acetal |
| 146 | 1-Decanol | Rhodalione |
| 147 | 2-Cyclohexen-1-one, 3-methyl-5-propyl- | Livescone |
| 148 | Phenol, 2-methyl-5-(1-methylethyl)- | Carvacrol |
| 149 | 2-Naphthalenol, decahydro- | Trans Deca Hydro Beta Naphthol |
| 150 | Cyclohexanol, 4-(1,1-dimethylethyl)-, acetate | Tertiary Butyl Cyclohexyl Acetate |
| 151 | 9-Decen-1-ol | Rosalva |
| 152 | Phenol, 5-methyl-2-(1-methylethyl)- | Thymol Nf |
| 153 | Cyclohexanol, 5-methyl-2-(1-methylethenyl)-, acetate, [1R-(1.alpha.,2.beta.,5.alpha.)] | Iso Pulegol Acetate |
| 154 | Benzene, [(3-methylbutoxy)methyl]- | Iso Amyl Benzyl Ether |
| 155 | 2(3H)-Furanone, 5-hexyldihydro-5-methyl- | Lactojasmon |
| 156 | Benzoic acid, butyl ester | Butyl Benzoate |
| 157 | Bicyclo[3.2.1]octan-8-one, 1,5-dimethyl-, oxime | Buccoxime |
| 158 | 2-Cyclopenten-1-one, 2-methyl-3-(2-pentenyl)- | Iso Jasmone |

In one aspect, suitable Table 2 perfume raw materials include perfume raw materials from number 1 to number 116 and mixtures thereof.

In one aspect, suitable Table 2 perfume raw materials include perfume raw materials from number 1 to number 79 and mixtures thereof.

In one aspect, suitable perfume raw materials having boiling point greater than 250° C. but less than or equal to 280° C. are those materials listed in Table 3 below and such materials are defined as Table 3 perfume raw materials.

TABLE 3

Perfumes

| Number | Registry Name | Trade Name |
|---|---|---|
| 1 | Dodecanenitrile | Clonal |
| 2 | Cyclohexanepropanoic acid, 2-propenyl ester | Allyl Cyclohexane Propionate |
| 3 | 2-Buten-1-one, 1-(2,6,6-trimethyl-2-cyclohexen-1-yl)- | Alpha Damascone |
| 4 | 1,4-Cyclohexanedicarboxylic acid, diethyl ester | Fructalate |
| 5 | 2(3H)-Furanone, 5-heptyldihydro- | Undecalactone |
| 6 | Naphthalene, 2-methoxy- | Beta Naphthol Methyl Ether |
| 7 | Benzenepropanal, 4-(1,1-dimethylethyl)- | Bourgeonal |
| 8 | 3-Cyclopentene-1-butanol, .beta.,2,2,3-tetramethyl- | Brahmanol |
| 9 | 1H-3a,7-Methanoazulen-6-ol, octahydro-3,6,8,8-tetramethyl-,[3R-(3.alpha.,3a.beta.,6.alpha.,7.beta.,8a.alpha.)]- | Cedrol |
| 10 | 2-Propen-1-ol, 3-phenyl-, acetate | Cinnamyl Acetate |
| 11 | Benzenepropanal, .alpha.-methyl-4-(1-methylethyl)- | Cymal |
| 12 | 2-Buten-1-one, 1-(2,6,6-trimethyl-1-cyclohexen-1-yl)-, (Z)- | Damascone Beta |
| 13 | 2-Buten-1-one, 1-(2,6,6-trimethyl-1,3-cyclohexadien-1-yl)- | Damascenone |
| 14 | 2-Buten-1-one, 1-(2,6,6-trimethyl-3-cyclohexen-1-yl)- | Delta Damascene |
| 15 | Butanoic acid, 1,1-dimethyl-2-phenylethyl ester | Dimethyl Benzyl Carbinyl Butyrate |
| 16 | 2-Dodecenal | 2 Dodecene-1-al |
| 17 | 2H-Pyran-2-one, 6-heptyltetrahydro- | Dodecalactone |
| 18 | Oxiranecarboxylic acid, 3-methyl-3-phenyl-, ethyl ester | Ethyl Methyl Phenyl Glycidate |
| 19 | Oxiranecarboxylic acid, 3-phenyl-, ethyl ester | Ethyl Phenyl Glycidate |
| 20 | Phenol, 2-methoxy-4-(2-propenyl)- | Eugenol |
| 21 | Benzenepropanal, .beta.-methyl-3-(1-methylethyl)- | Florhydral |
| 22 | Benzenepropanal, 2-ethyl-.alpha.,.alpha.-dimethyl- | Floralozone |
| 23 | 4,7-Methano-1H-inden-6-ol, 3a,4,5,6,7,7a-hexahydro-, propanoate | Frutene |
| 24 | 2,6-Octadienenitrile, 3,7-dimethyl-, (E)- | Geranyl Nitrile |
| 25 | 1,3-Benzodioxole-5-carboxaldehyde | Heliotropin |
| 26 | Ionone | Ionone Ab |
| 27 | 3-Buten-2-one, 4-(2,6,6-trimethyl-2-cyclohexen-1-yl)-, (E)- | Ionone Alpha |
| 28 | 3-Buten-2-one, 4-(2,6,6-trimethyl-1-cyclohexen-1-yl)- | Ionone Beta |
| 29 | 3-Buten-2-one, 4-(2,6,6-trimethyl-1-cyclohexen-1-yl)-, (E)- | Ionone Beta |
| 30 | 3-Buten-2-one, 3-methyl-4-(2,6,6-trimethyl-2-cyclohexen-1-yl)- | Ionone Gamma Methyl |
| 31 | 2-Buten-1-one, 1-(2,4,4-trimethyl-2-cyclohexen-1-yl)-, (E)- | Isodamascone N |
| 32 | Phenol, 2-methoxy-4-(1-propenyl)- | Iso Eugenol |
| 33 | 2H-Pyran-4-ol, tetrahydro-3-pentyl-, acetate | Jasmal |
| 34 | Bicyclo[3.1.1]hept-2-ene-2-ethanol, 6,6-dimethyl-, acetate | Nopyl Acetate |
| 35 | Benzenepropanol, .alpha.,.alpha.-dimethyl-, acetate | Phenyl Ethyl Dimethyl Carbinyl Acetate |
| 36 | Propanoic acid, 2-methyl-, 3a,4,5,6,7,7a-hexahydro-4,7-methano-1H- | Cyclabute |
| 37 | Benzaldehyde, 4-hydroxy-3-methoxy- | Vanillin |
| 38 | 3-Cyclohexene-1-carboxaldehyde, 1-methyl-4-(4-methylpentyl)- | Vernaldehyde |
| 39 | Benzenemethanol, ar-methoxy-, acetate | Anisyl Acetate |
| 40 | Bicyclo[2.2.1]hept-5-ene-2-carboxylic acid, 3-(1-methylethyl)-,ethyl ester, (2-endo,3-exo)- | Herbanate Ci |
| 41 | Butanoic acid, 3-methyl-, 2-phenylethyl ester | Beta Phenyl Ethyl Isovalerate |
| 42 | Benzenepropanal, 4-methoxy-.alpha.-methyl- | Canthoxal |
| 43 | Bicyclo[7.2.0]undec-4-ene, 4,11,11-trimethyl-8-methylene-,[1R-(1R*,4E,9S*)]- | Caryophyllene Extra |
| 44 | Cyclohexenebutanal, .alpha.,2,2,6-tetramethyl- | Cetonal |
| 45 | 2-Propen-1-ol, 3-phenyl- | Cinnamic Alcohol |
| 46 | 6-Octen-1-ol, 3,7-dimethyl-, propanoate | Citronellyl Propionate |
| 47 | Propanoic acid, decyl ester | N-Decyl Propionate |
| 48 | Phenol, 2-methoxy-4-propyl- | Dihydro Eugenol |

TABLE 3-continued

Perfumes

| Number | Registry Name | Trade Name |
|---|---|---|
| 49 | Cyclohexanol, 1-ethenyl-2-(1-methylpropyl)-, acetate | Dihydro Ambrate |
| 50 | 2-Propenoic acid, 3-phenyl-, ethyl ester | Ethyl Cinnamate |
| 51 | Butanoic acid, 3,7-dimethyl-2,6-octadienyl ester, (E)- | Geranyl Butyrate |
| 52 | 2-Octanol, 8,8-dimethoxy-2,6-dimethyl- | Hydroxycitronellal Dimethyl Acetal |
| 53 | Cyclohexadieneethanol, 4-(1-methylethyl)-, formate | Iso Bergamate |
| 54 | Dodecanal | Lauric Aldehyde |
| 55 | Propanoic acid, 2-methyl-, 1-ethenyl-1,5-dimethyl-4-hexenyl ester | Linalyl Iso Butyrate |
| 56 | Benzenepropanol, .beta.,.beta.,3-trimethyl- | Majantol |
| 57 | Benzene, 1,2-dimethoxy-4-(2-propenyl)- | Methyl Eugenol |
| 58 | Propanoic acid, 2-methyl-, 2-phenylethyl ester | Phenyl Ethyl Iso Butyrate |
| 59 | 2-Propenenitrile, 3-phenyl- | Cinnamalva |
| 60 | Benzene, [2-(1-propoxyethoxy)ethyl]- | Acetal R |
| 61 | 9-Undecenal, 2,6,10-trimethyl- | Adoxal |
| 62 | 2-Naphthalenol, 1,2,3,4,4a,5,6,7-octahydro-2,5,5-trimethyl- | Ambrinol 20t |
| 63 | 2-Naphthalenol, octahydro-2,5,5-trimethyl- | Ambrinol 20t |
| 64 | Ethanol, 2-[(1,7,7-trimethylbicyclo[2.2.1]hept-2-yl)oxy]-, exo- | Arbanol |
| 65 | 1H-2-Benzopyran, 3,4,4a,5,8,8a(or 3,4,4a,7,8,8a)-hexahydro-3,3,6,7- | Bigarade Oxide |
| 66 | Cyclohexene, 4-(1,5-dimethyl-4-hexenylidene)-1-methyl- | Bisabolene |
| 67 | 1H-3a,7-Methanoazulene, octahydro-6-methoxy-3,6,8,8-tetramethyl-,[3R-(3.alpha.,3a.beta.,6.alpha.,7.beta.,8a.alpha.)]- | Cedramber |
| 68 | Phenol, 4-chloro-3,5-dimethyl- | 4-Chloro 3,5 Xylenol |
| 69 | 2,6-Octadiene, 1,1-diethoxy-3,7-dimethyl- | Citrathal |
| 70 | Acetaldehyde, [(3,7-dimethyl-6-octenyl)oxy]- | Citronellyl Oxyacetaldehyde |
| 71 | Benzenepropanenitrile, .alpha.-ethenyl-.alpha.-methyl- | Citrowanil B |
| 72 | Cyclohexanol, 2-(1,1-dimethylpropyl)-, acetate | Coniferan |
| 73 | 2H-1-Benzopyran-2-one | Coumarin |
| 74 | 1,3-Nonanediol, monoacetate | Diasmol |
| 75 | Benzene, 1,1'-methylenebis- | Diphenyl Methane |
| 76 | Benzene, 1,1'-oxybis- | Diphenyl Oxide |
| 77 | 1,6-Octadiene, 3-(1-ethoxyethoxy)-3,7-dimethyl- | Elinthal |
| 78 | Cyclopentanone, 2-heptyl- | Fleuramone |
| 79 | 5,8-Methano-2H-1-benzopyran-2-one, 6-ethylideneoctahydro- | Florex |
| 80 | Octanoic acid, 2-acetyl-, ethyl ester | Gelsone |
| 81 | Indeno[1,2-d]-1,3-dioxin, 4,4a,5,9b-tetrahydro- | Indoflor Crist. |
| 82 | Benzeneacetic acid, 2-methylpropyl ester | Iso Butyl Phenylacetate |
| 83 | 2,6-Nonadienenitrile, 3,7-dimethyl- | Lemonile |
| 84 | 3-Decanone, 1-hydroxy- | Methyl Lavender Ketone |
| 85 | Undecane, 1,1-dimethoxy-2-methyl- | Methyl Nonyl Acetaldehyde Dimethyl Aceta |
| 86 | 1-Propanone, 1-[2-methyl-5-(1-methylethyl)-2-cyclohexen-1-yl]- | Nerone |
| 87 | 5,9-Undecadienal, 2,6,10-trimethyl- | Oncidal |
| 88 | Quinoline, 6-methyl- | Para Methyl Quinoline |
| 89 | Propanoic acid, 2-methyl-, 2-phenoxyethyl ester | Phenoxy Ethyl Iso Butyrate |
| 90 | Ethanol, 2-phenoxy-, propanoate | Phenoxy Ethyl Propionate Formerly N-225 |
| 91 | 4,7-Methano-1H-indene-2-carboxaldehyde, octahydro-5-methoxy- | Scentenal |
| 92 | 9-Undecen-2-one, 6,10-dimethyl- | Tetra Hydro Psuedo Ionone |
| 93 | Benzenemethanol, .alpha.-(trichloromethyl)-, acetate | Trichloromethyl Phenyl Carbinyl Acetate |
| 94 | Phenol, 2-methoxy-4-(methoxymethyl)- | Vaniwhite |
| 95 | Bicyclo[2.2.2]oct-5-ene-2-carboxaldehyde, 6-methyl-8-(1-methylethyl)- | Maceal |
| 96 | Benzene, [2-(3-methylbutoxy)ethyl]- | Phenyl Ether Isamyl Ether (Aka Anther) |
| 97 | 2-Cyclohexene-1-carboxylic acid, 2,3,6,6-tetramethyl-, ethyl ester | Givescone |

In one aspect, suitable Table 3 perfume raw materials include perfume raw materials from number 1 to number 58 and mixtures thereof.

In one aspect, suitable Table 3 perfume raw materials include perfume raw materials from number 1 to number 39 and mixtures thereof.

In one aspect, suitable perfume raw materials may be selected from the group consisting of 4-methoxybenzaldehyde; 4-phenylbutan-2-one; 3,7-dimethyl-2-methylene-6-octenal; 4-(2,6,6-trimethyl cyclohex-1-ene-1-yl)but-3-ene-2-one; 2,4-dimethylcyclohex-3-ene-1-carbaldehyde; 2-methyl-3-(paraisopropylphenyl)propionaldehyde; 2-Buten-1-one, 1-(2,6,6-trimethyl-1,3-cyclohexadien-1-yl)-; 1-cyclohexyl-ethylene-crotonate; 1-(2,6,6-trimethyl-3-cyclohexen-1-yl)-2-buten-1-one; 3-methyl cyclopentadecenone; 4-(2,6,6-trimethyl-1-cyclohexenyl)butan-2-one; 2,5-Dimethyl-2-octen-6-one dihydro-nor-cyclopentadienyl acetate; 3-(o-(and p-)ethylphenyl)-2,2-dimethylpropionaldehyde; 3-(3-isopropylphenyl)butanal; 3-Buten-2-one, 3-methyl-4-(2,6,6-trimethyl-2-cyclohexen-1-yl)-; alpha-methyl-3,4(methylenedioxy)hydrocinnamaldehyde; n-hexyl ortho hydroxy benzoate; 7-acetyl-1,2,3,4,5,6,7,8-octahydro-1,1,6,7,tetramethyl naphthalene; 4-(1-Ethoxyvinyl)-3,3,5,5-tetramethyl-cyclohexan-1-one; 2-Cyclohexen-1-one, 2-methyl-5-(1-methylethenyl)-, (R)-; 2,4-Dimethyl-3-cyclohexene-1-carboxaldehyde; 3,7-dimethyl-1,6-octadien-3-ol; 2,6-Dimethyl-5-Heptenal; Methyl Dihydro Jasmonate; Methyl Nonyl Acetaldehyde; 6,6-dimethoxy-2,5,5-trimethylhex-2-ene; 2-Cyclohexen-1-one, 2-methyl-5-(1-methylethenyl)-, (R)-; Octaldehyde; 2-Cyclohexyl-1,6-heptadien-3-one and mixtures thereof.

Suitable polymeric materials may comprise at least two moieties each of which may be independently selected from the group consisting of carboxylic acid, hydroxyl, ester, amide, amine, nitrile and thiol moieties.

In one aspect, said polymeric compound comprises, per polymeric compound, at least two moieties selected from the moieties consisting of a carboxylic acid moiety, an amine moiety, a hydroxyl moiety, and a nitrile moiety. In one aspect, the polymeric material contains two or more carboxylic acid moieties on each polymeric molecule. In one aspect, polymeric materials may contain a backbone of polybutadiene, polyisoprene, polybutadiene/styrene, polybutadiene/acrylonitrile, carboxyl-terminated polybutadiene/acrylonitrile or combinations thereof. In another aspect, suitable polymeric materials encompass amine terminated, epoxy terminated, or vinyl terminated polymers. Suitable molecular weights for these polymers range from about 1,000 to about 10,000,000. In one aspect, the suitable polymers may have molecular weights that range from about 1,000 to about 10,000,000 or from about 2,000 to about 50,000. Suitable polymeric materials are available from NOVEON (Cleveland, Ohio U.S.A) and SARTOMER (Philadelphia, Pa. U.S.A.). Such materials include HYCAR® materials CTB 2000×162, CTBNX 1300×18, CTBNX 1300×9, CTBN 1300×8, CTBN 1300×31, ATB 2000×173, ATBN 1300×21, ATBN 1300×16, ATBN 1300×45, ATBN 1300×35, ATBN 1300×42, VTB 2000×168, VTBNX1300×33, VTBNX1300×43, ETBN 1300×40, and ETBN 1300×44 from NOVEON or Emerald Performance Materials of Cuyahoga Falls, Ohio U.S.A. and Krasol® LBH 5000 from SARTOMER.

In one aspect, the benefit delivery composition may comprise a cross-linker. In any aspect, such cross-linker may provide covalent cross-linking and/or ionic cross-linking. In one aspect, the benefit agent delivery composition comprises a cross-linker at a concentration similar to the equivalence of the polymeric material. In one aspect, the equivalence ratio of cross-linker equivalence to the carboxylic acid equivalence within the composition is from about 0.5 to about 2.0. In one aspect, the equivalence ratio is from about 0.8 to about 1.2. The cross-linker can be any material that provides cross-linking when placed in the presence of the carboxylic acid containing polymer. Suitable cross-linkers include polyamines, epoxides and polycarbodiimides. In one aspect, the polycarbodiimide cross-linker compound may be ZOLDINE™ XL-29SE manufactured by Angus Chemical Company, a subsidiary of the Dow Chemical Company of Midland, Mich. U.S.A. In one aspect, polyamines may comprise diethylenetriamine, polyethyleneimines, polyvinylamines, and/or ethylene diamine moieties.

In one aspect, the crosslinker comprises a polyamine that may comprise diethylenetriamine, ethylene diamine, polyethyleneimine, polyvinylamine, bis(3-aminopropyl)piperazine, N,N-Bis-(3-aminopropyl)methylamine, tris(2-aminoethyl)amine or mixtures thereof.

Suitable polyamines include Lupasol® WF, SK, PS, PO100, P, HF, G500, G35, G20 water free, G20, G100, FG, FC, and PR8515 products supplied by BASF of Ludwigshaven, Germany.

Other materials may be added to the benefit agent delivery compositions disclosed herein. For example, colorants can be added to such benefit agent delivery compositions including dyes and pigments. The colorant may be one or more oil soluble dyes. Such dyes may be added to the benefit agent prior to the formation of the benefit agent delivery compositions disclosed herein. Antioxidants may be added to benefit agent delivery compositions disclosed herein. Such antioxidants may protect benefit agents, including fragrances from oxidation. Suitable antioxidants include BHA supplied by Eastman Chemical Company of Kingsport Tenn. U.S.A. UV inhibitors can be added to benefit agent delivery compositions disclosed herein and may prevent discoloration. Suitable UV inhibitors include TINUVIN® commercial products supplied by Ciba® of Basel, Switzerland.

Other materials maybe added to the benefit agent delivery compositions disclosed herein are materials that will help to process the benefit agent delivery compositions like solvents, diluents, surfactants, fatty acids, polymers, suitable materials are diluents like benzylbenzoate, nonionic surfactants like TAE80, fatty acids like coconut oil, polymers like PEG4000.

In one aspect, the benefit agent delivery compositions of the present invention may be clear. However, such compositions may also be opaque. Such compositions can be made opaque by the addition of opacifying agents. Suitable opacifying agents include titanium dioxide, zinc oxide, inorganic salts, waxes, water, and other organic opacifiers that are well known to those of skilled in the art.

Additional materials may be added to the benefit agent delivery compositions disclosed herein. Such materials may or may not be volatile. Such materials include solvents, oils, esters, phthalates, fatty acids, triglycerides, ethers, oils, aliphatic materials, hydrocarbons, plasticizers, and alcohols. Such materials may or may not be hydrophilic. Suitable hydrophilic materials include water, glycols, and alcohols. In one aspect, surfactants may be added to the benefit agent delivery compositions disclosed herein. Suitable surfactants include nonionic, anionic, cationic, and amphoteric surfactants—examples of which will be well known to those of skill in the art. The inclusion of surfactants may facilitate the inclusion of hydrophilic materials into the benefit agent delivery compositions disclosed herein.

Process of Making Benefit Agent Delivery Compositions

The benefit agent delivery compositions disclosed in the present application may be made via the teachings of USPA 2006/0067963 A1, and the examples disclosed herein.

The benefit agent containing compositions disclosed in the present application may be processed in accordance with the teachings of U.S. Pat. Nos. 6,451,751 B1, 6,972,276 B1, 6,764,986 B1, 6,740,713 B1 and the examples disclosed herein. Suitable forms for such benefit agent delivery compositions include, solids and fluids including agglomerates, emulsions, solutions, prills, beads and encapsulates. When employed to product a benefit agent delivery composition the particle size of the benefit agent delivery composition in said agglomerates, emulsions, solutions, prills, beads and encapsulates may be from about 0.1 microns to about 100 microns, from about 1 micron to about 60 microns or even from about 5 to about 40 microns. In addition to the foregoing, the benefit agent delivery compositions of the present invention may be further processed in accordance with the teachings of published US Patent Application No. 2007/0196502 A1 to yield a particle wherein the benefit agent delivery composition comprises at least a portion or even all of one or more layers of the resulting particle.

In one aspect, a method for making a benefit agent delivery composition comprising:
 a.) mixing a first mixture, wherein said first mixture comprises: from about 15% to about 95% by weight of a volatile hydrophobic liquid; and from about 3% to about 40% by weight of a polymeric compound containing a carboxylic acid, until said first mixture is completely mixed; and mixing into said first mixture, from about 1.5% to about 40% by weight of a cross-linking agent; or
 b.) mixing a first mixture, wherein said first mixture comprises: from about 15% to about 95% by weight of a volatile hydrophobic liquid; and from about 3% to about 40% by weight of a polymeric compound containing a carboxylic acid, until said first mixture is completely mixed; and mixing into said first mixture, from about 0% to about 40% by weight of a cross-linking agent; or
 c.) mixing a first mixture, wherein said first mixture comprises: from about 15% to about 95% by weight of a volatile hydrophobic liquid; and from about 3% to about 40% by weight of a polymeric compound containing a carboxylic acid, until said first mixture is completely mixed; and mixing into said first mixture a second mixture, wherein said second mixture comprises: from 15% to about 95% by weight volatile hydrophobic liquid; and from about 1.5% to about 40% by weight of a cross-linking agent; or
 d.) combining from about 15% to about 95% by weight of a volatile hydrophobic liquid; and from about 3% to about 40% by weight of a polymeric compound containing a carboxylic acid, until said first mixture is completely mixed; and mixing into said first mixture, from about 0% to about 40% by weight of a cross-linking agent;
 e.) optionally combining the mixtures produced in a.), b.), c.) and/or d.) with a diluent and/or a surfactant; and/or further processing the mixtures produced in a.), b.), c.) and/or d.) to form a particle, bead and/or agglomerate is disclosed.

In one aspect, the benefit agent delivery composition is pre-made and added to a consumer.

In one aspect the components of the benefit agent delivery composition are added separately to a consumer product and the benefit agent delivery composition may form in the consumer before, during and/or after use by the consumer.

In one aspect, when additional benefit agent(s) and/or benefit agent delivery system(s), for example perfume and/or encapsulated perfume, are employed to form a particle, bead and/or agglomerate, the benefit agent delivery composition of the present invention may be added before, during or after said additional benefit agent(s) and/or benefit agent delivery system(s) are added to said a particle, bead and/or agglomerate.

In one aspect, when additional benefit agent(s) and/or benefit agent delivery system(s), for example perfume and/or encapsulated perfume, are employed, the benefit agent delivery composition of the present invention may be added before, during or after said additional benefit agent(s) and/or benefit agent delivery system(s) are added to a consumer.

Suitable equipment for use in the processes disclosed herein may include continuous stirred tank reactors, homogenizers, turbine agitators, recirculating pumps, paddle mixers, ploughshear mixers, ribbon blenders, vertical axis granulators, twin screw extruders and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., USA), Arde Barinco (New Jersey, USA), Wenger (Sabetha, Kans. USA).

Compositions Comprising Benefit Agent Delivery Compositions

Applicants' compositions comprise an embodiment of the benefit agent delivery compositions disclosed in the present application. In one aspect, such compositions may be a consumer product. While the precise level of benefit agent delivery composition that is employed depends on the type and end use of the product comprising such composition, a products, including cleaning and/or fabric treatment products, may comprise, based on total product weight, from about 0.001% to about 25%, from about 0.01% to about 5%, or even from about 0.05% to about 3% benefit agent delivery composition.

In one aspect, a consumer product comprising at least one embodiment of a benefit agent delivery composition disclosed herein and a material selected from the group consisting of a surfactant, an enzyme, a polymer, a dye, a neat perfume, a perfume delivery system in addition to Applicants' benefit agent delivery system and mixtures thereof is disclosed. Suitable perfume delivery systems are described in published U.S. Patent Application No. 2007/0275866 A1

Aspects of the invention include the use of the benefit agent delivery compositions of the present invention in laundry detergent compositions (e.g., TIDE™), hard surface cleaners (e.g., MR CLEAN™), automatic dishwashing liquids (e.g., CASCADE™), dishwashing liquids (e.g., DAWN™), and floor cleaners (e.g., SWIFFER™). Non-limiting examples of cleaning compositions may include those described in U.S. Pat. Nos. 4,515,705; 4,537,706; 4,537,707; 4,550,862; 4,561, 998; 4,597,898; 4,968,451; 5,565,145; 5,929,022; 6,294,514; 6,376,445, 7,169,741 B2 and 7,297,674 B2 as well as in U.S. Patent Application Publication No. 2005/0130864 A1. The cleaning compositions disclosed herein may be formulated such that, during use in aqueous cleaning operations, the wash water will have a pH of between about 5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Fabric treatment compositions disclosed herein typically comprise a fabric softening active ("FSA"). Suitable fabric softening actives, include, but are not limited to, materials selected from the group consisting of quats, amines, fatty esters, sucrose esters, silicones, dispersible polyolefins, clays, polysaccharides, fatty oils, polymer latexes and mixtures thereof.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' delivery particles and FSAs. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, thickeners/structurants, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, thickeners/structurants, fabric softeners, carriers, hydrotropes, processing aids and/or pigments. However, when one or more adjuncts is present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Suitable thickeners/structurants and useful levels of same are described in U.S. Patent Application Publication No. 2005/0130864 A1 and U.S. Pat. Nos. 7,169,741 B2 and 7,297,674 B2.

Processes of Making and Using Compositions

The compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

Compositions containing the benefit agent delivery composition disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Packaging Comprising Benefit Agent Delivery Compositions

In one aspect, packaging comprising the benefit agent delivery compositions is disclosed. Such packaging may be used to package a product such as a consumer product. The benefit delivery compositions of the present invention may be adhered or attached any where on such packaging. Such packaging may take any form including wrapping, or a container. In one aspect, a benefit agent delivery composition disclosed herein may be adhered or attached to the exterior and/or the interior surface of such packaging. In one aspect, said packaging may comprise a container comprising a cap and said benefit agent delivery composition disclosed herein is adhered or attached to the exterior or interior surface of said cap.

Displays Comprising Benefit Agent Delivery Compositions

In one aspect, a display comprising the benefit agent delivery compositions is disclosed. Such display may be used to attract attention to, market and/or assist in whole or in part the sale of a product such as a consumer product. The benefit delivery compositions of the present invention may be adhered or attached any where on such display. Such display may take any form including posters, sales and/or marketing literature, or a container. In one aspect, a benefit agent delivery composition disclosed herein is adhered or attached to the exterior and/or the interior surface of such display.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

Equal amounts a perfume composition and amine-terminated Hycar® ATBN1300X42 from Noveon are weighted and mixed for five minutes using a Ultra-Turrax as needed. The ingredients are put at 60° C. in warm water bath for 1 hour before use/mixing. After mixing the mixture is put in a warm water bath at 60° C. for ±12 hours. A homogenous, viscous and sticky material is obtained.

In the same way as described above different ratios between the components can be used:

| | Weight % | | | | |
|---|---|---|---|---|---|
| Perfume composition | 40 | 50 | 60 | 70 | 80 |
| Hycar ® 1300X42 | 60 | 50 | 40 | 30 | 20 |

Example 2

A mixture comprising 50% of a perfume composition, 40% of carboxyl-terminated Hycar® 1300×18 (CAS#0068891-50-9) from Noveon, (put at 60° C. in warm water bath for 1 hour before mixing) and 10% of Lupasol® WF (CAS#09002-98-6) from BASF (put at 60° C. in warm water bath for 1 hour before mixing). Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

In the same way as described above different ratios between the components can be used:

| | Weight % | | | | |
|---|---|---|---|---|---|
| Perfume composition | 40 | 50 | 60 | 70 | 80 |
| Lupasol ® WF | 12 | 10 | 8 | 6 | 4 |
| Hycar ® CTBN1300X18 | 48 | 40 | 32 | 24 | 16 |

| | Weight % | | | | | | | |
|---|---|---|---|---|---|---|---|---|
| Perfume composition | 50 | 50 | 50 | 50 | 50 | 50 | 50 | 50 |
| Lupasol ® WF | 2.5 | 5 | 7.5 | 10 | 12.5 | 15 | 17.5 | 20 |
| Hycar ® CTBN 1300X18 | 47.5 | 45 | 42.5 | 40 | 37.5 | 35 | 32.5 | 30 |

Example 3

A mixture comprising 50% of a perfume composition, 40% of carboxyl-terminated Hycar® CTBN 1300×18 from Noveon (put at 60° C. in warm water bath for 1 hour before mixing) and 10% of Lupasol® WF (CAS#09002-98-6) from BASF (put at 60° C. in warm water bath for 1 hour before use) is formed.

Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

Example 4

In a first step of the preparation the Lupasol® WF (CAS#09002-98-6) from BASF 15% is used in combination with 35% of carboxyl-terminated Hycar® CTBN1300X18 and 17% of this polymer mix is diluted with 83% of Benzyl Benzoate to make a workable solution. The materials described above are put together, in the ratio's described above, in a glass jar at 80° C. on a hot plate with stirring using a magnetic stirrer. Next the polymer premix is mixed with a perfume composition in a 1:1 ratio. This polymer—perfume mix is than added to a fabric enhancer composition.

Example 5

Agglomeration of Benefit Agent Delivery Composition

Perfume System for Use in Powder Detergents

Starting from any of Examples 1 to 3 as described above:
The resulting homogenous, viscous and sticky material is held at 60° for ±2 hours before starting the agglomeration process. Next, a mixture comprising 40% of the viscous, sticky sample and 60% of melted TAE80 is formed by combining and mixing with an Ultra-Turrax T25 Basic equipment (from IKA) for 5 to 10 minutes. Then, 1 part of the TAE80/sticky sample is very slowly added to 0.6 parts of light soda ash using a Braun kitchen robot to form agglomerates. The resulting agglomerates are then used in a powder detergent.

Example 6

Liquid Application

Starting from any of Examples 1 to 3 as described above:
The resulting homogenous, viscous and sticky material is held at 60° for ±2 hours before starting the dilution process.

| | Weight % | | | | |
|---|---|---|---|---|---|
| Sticky sample | 20 | 30 | 40 | 50 | 60 |
| Benzyl benzoate or fatty acid | 80 | 70 | 60 | 50 | 40 |

The viscous sticky material obtained as described in any of Examples 1-3 above are mixed at different ratios for five minutes using an Ultra-Turrax T25 Basic equipment (from IKA), at the levels listed in the table above, with benzyl benzoate before the resulting mixture is a added to a liquid detergent.

Example 7

Different Process Manner of Obtaining the Consumer Benefit Delivery Agent System Addition of the different ingredients without premixing of the materials:
The following are mixed without premixing/premixtures being formed.

| | Weight % | | | |
|---|---|---|---|---|
| Perfume composition | 40 | 50 | 60 | 70 |
| Lupasol ® wf Via premix in H$_2$O (50%/50%) | 12 | 10 | 8 | 6 |
| Hycar ® CTBN 1300X18 Via premix in Benzyl Benzoate (20%/80% Benzyl Benzoate) | 48 | 40 | 32 | 24 |

Example 8

Non-limiting examples of product formulations containing a benefit agent delivery composition are summarized in the following table.

| | | EXAMPLES | | | | | | | | |
|---|---|---|---|---|---|---|---|---|---|---|
| (% wt) | | XI | XII | XIII | XIV | XV | XVI | XVII | XVIII | XIX | XX |
| FSA $^a$ | | 14 | 16.47 | 14 | 12 | 12 | 16.47 | — | — | 5 | 5 |
| FSA $^b$ | | | | | | | | 3.00 | — | — | — |
| FSA $^c$ | | | | | | | | | 6.5 | — | — |

-continued

| (% wt) | XI | XII | XIII | XIV | XV | XVI | XVII | XVIII | XIX | XX |
|---|---|---|---|---|---|---|---|---|---|---|
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch $^d$ | 1.25 | 1.47 | 2.00 | 1.25 | — | 2.30 | 0.5 | 0.70 | 0.71 | 0.42 |
| Benefit agent delivery composition | 0.6 | 0.75 | 0.6 | 0.75 | 0.37 | 0.60 | 0.37 | 0.6 | 0.37 | 0.37 |
| Phase Stabilizing Polymer $^f$ | 0.21 | 0.25 | 0.21 | 0.21 | 0.14 | — | — | 0.14 | — | — |
| Suds Suppressor $^g$ | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA $^h$ | 0.017 | 0.017 | 0.017 | 0.017 | 0.007 | 0.007 | 0.20 | — | 0.002 | 0.002 |
| Preservative (ppm) $^{i,j}$ | 5 | 5 | 5 | 5 | 5 | 5 | — | 250 $^j$ | 5 | 5 |
| Antifoam $^k$ | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant $^l$ | 0.01 | 0.01 | 0.01 | 0.01 | 0.01 | 0.01 | 0.01 | 0.01 | 0.01 | 0.01 |
| Neat Perfume | 0.8 | 0.7 | 0.9 | 0.5 | 1.2 | 0.5 | 1.1 | 0.6 | 1.0 | 0.9 |
| Deionized Water | * | * | * | * | * | * | * | * | * | * |

* Balance
$^a$ N,N-di(tallowoyloxyethyl)-N,N-dimethylammonium chloride.
$^b$ Methyl bis(tallow amidoethyl)2-hydroxyethyl ammonium methyl sulfate.
$^c$ Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
$^d$ Cationic high amylose maize starch available from National Starch under the trade name CATO ®.
$^f$ Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
$^g$ SE39 from Wacker
$^h$ Diethylenetriaminepentaacetic acid.
$^i$ KATHON ® CG available from Rohm and Haas Co. "PPM" is "parts per million."
$^j$ Gluteraldehyde
$^k$ Silicone antifoam agent available from Dow Corning Corp. under the trade name DC2310.
$^l$ Hydrophobically-modified ethoxylated urethane available from Rohm and Haas under the tradename Aculan 44.

Example 9

Benefit Agent Delivery Composition in Dry Laundry Formulations

| Component | % w/w granular laundry detergent composition | | | | | | |
|---|---|---|---|---|---|---|---|
|  | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroxyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |

-continued

| Component | % w/w granular laundry detergent composition | | | | | | |
|---|---|---|---|---|---|---|---|
| | A | B | C | D | E | F | G |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Benefit agent delivery composition | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc. | 0.1 | 0.1 | 0.1 | 0.1 | 0.1 | 0.1 | 0.1 |
| Total Parts | 100 | 100 | 100 | 100 | 100 | 100 | 100 |

Example 10

Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3 - Methyl -1,3- propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Benefit Agent Delivery Composition | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product composition comprising:
   a.) from about 0.001% to about 10% of a consumer benefit agent delivery composition comprising:
      (i) from about 5% to about 95% by weight of a benefit agent;
      (ii) from about 5% to about 70% by weight of a polymeric compound, wherein said polymeric compound is a polybutadiene/acrylonitrile polymer;
      (iii) from greater than 0% to about 50% by weight of a cross-linking agent comprising a polyamine;
      wherein the ratio of said polymeric compound to said cross-linking agent is from about 0.5 to about 2.0;
      said consumer benefit agent delivery composition comprising ionic cross-links between said benefit agent and said polymeric compounds, said cross-linking being provided by said crosslinker; and
   b.) a consumer product ingredient,
   wherein said consumer product is a hard surface cleaner, a fabric care composition, a liquid laundry detergent or a solid laundry detergent.

2. A consumer product composition according to claim 1 comprising:
   a.) from about 0.001% to about 10% of a consumer benefit agent delivery composition comprising:
      (i) from about 30% to about 85% by weight of a benefit agent;
      (ii) from about 20% to about 60% by weight of a polymeric compound wherein said polymeric compound is a polybutadiene/acrylonitrile polymer;
      (iii) from greater than 0% to about 10% by weight of a cross-linking agent comprising a polyamine, wherein said polyamine comprises diethylenetriamine, ethylene diamine, polyethyleneimine, polyvinylamine, bis(3-aminopropyl)piperazine, N,N-Bis-(3-aminopropyl)methylamine, tris(2-aminoethyl)amine or mixtures thereof;
      wherein the ratio of said polymeric compound to said cross-linking agent is from about 0.5 to about 2.0; and
   b.) a consumer product ingredient.

3. A consumer product composition according to claim 2 comprising:
   a.) from about 0.001% to about 10% of a consumer benefit agent delivery composition comprising:
      (i) from about 40% to about 60% by weight of a benefit agent;
      (ii) from about 30% to about 55% by weight of a polymeric compound wherein said polymeric compound is a polybutadiene/acrylonitrile polymer;
      (iii) from about 1% to about 7% by weight of a cross-linking agent;
   wherein the ratio of said polymeric compound to said cross-linking agent is from about 0.5 to about 2.0; and
   b.) a consumer product ingredient.

4. The composition of claim 1, wherein said benefit agent is selected from the group consisting of a perfume raw material, a fragrance, a perfume, an essential oil, an insecticide, an insect repellant, a pesticide, a herbicide, an odorant, a malodor counteractant, an odor masking agent, a cooling agent, a vitamin, softening agent, a skin care agent, a silicone, a softening agent, an encapsulated perfume and combinations thereof.

5. The composition of claim 2, wherein said benefit agent is selected from the group consisting of a fragrance, a perfume, an essential oil, an insecticide, an insect repellant, a pesticide, a herbicide, an odorant, a malodor counteractant, an odor masking agent, a cooling agent, a vitamin, softening agent, a skin care agent, a silicone, a softening agent, an encapsulated perfume and combinations thereof.

6. The composition of claim 3, wherein said benefit agent is selected from the group consisting of a fragrance, a perfume, an essential oil, an insecticide, an insect repellant, a pesticide, a herbicide, an odorant, a malodor counteractant, an odor masking agent, a cooling agent, a vitamin, softening agent, a skin care agent, a silicone, a softening agent, an encapsulated perfume and combinations thereof.

7. A consumer product comprising a composition according to claim 1 and packaging, said composition being attached or adhered to said packaging.

* * * * *